United States Patent [19]

Du Vernet

[11] Patent Number: 4,514,335

[45] Date of Patent: Apr. 30, 1985

[54] $C_{21}$-DICARBOXYLIC ACID ISETHIONATES AS PRIMARY ANIONIC SURFACTANTS

[75] Inventor: Richard B. Du Vernet, Mt. Pleasant, S.C.

[73] Assignee: Westvaco Corporation, New York, N.Y.

[21] Appl. No.: 532,698

[22] Filed: Sep. 16, 1983

Related U.S. Application Data

[62] Division of Ser. No. 395,252, Jul. 6, 1982, Pat. No. 4,476,055.

[51] Int. Cl.³ .................... C07C 143/90; C11D 1/28
[52] U.S. Cl. .................................. 260/400; 560/127
[58] Field of Search ........................ 560/127; 260/400

[56] References Cited

U.S. PATENT DOCUMENTS

| | | | |
|---|---|---|---|
| Re. 29,337 | 8/1977 | Ward | 252/108 |
| 1,906,484 | 5/1933 | Nuesslein . | |
| 2,781,321 | 2/1957 | Mayhew et al. | 252/161 |
| 2,894,912 | 7/1959 | Geitz | 252/121 |
| 3,228,980 | 1/1966 | Weil et al. | 260/400 X |
| 3,383,396 | 5/1968 | Cahn et al. | 260/400 |
| 3,385,373 | 5/1968 | Caldwell | 260/400 |
| 3,385,873 | 5/1968 | Caldwell | 260/400 |
| 3,394,155 | 7/1968 | Cahn et al. | 260/400 |
| 3,420,857 | 1/1969 | Holland et al. | 260/400 |
| 3,420,858 | 1/1969 | McCrimlisk | 260/400 |
| 3,753,968 | 8/1973 | Ward | 260/97.6 |
| 3,842,119 | 10/1974 | Bills | 260/468 K |
| 3,862,049 | 1/1975 | McGrath et al. | 252/108 |
| 3,879,309 | 4/1975 | Gatti et al. | 252/117 |
| 4,092,259 | 5/1978 | Prince | 252/117 |
| 4,092,260 | 5/1978 | Prince | 252/117 |
| 4,096,082 | 6/1978 | Prince | 252/117 |
| 4,180,470 | 12/1979 | Tokosh et al. | 252/121 |
| 4,405,526 | 9/1983 | Lamberti et al. | 260/400 |

FOREIGN PATENT DOCUMENTS 1059984 2/1967 United Kingdom .

*Primary Examiner*—Helen M. S. Sneed
*Attorney, Agent, or Firm*—Terry B. McDaniel; Richard L. Schmalz

[57] ABSTRACT

Disclosed are novel water-soluble surfactants prepared by reacting 2-hydroxyethane sulfonate with $C_{21}$-dicarboxylic acid or a mixture of $C_{21}$-dicarboxylic acid and fatty acids wherein the $C_{21}$-dicarboxylic acid comprises at least 5% by weight of the mixture, the $C_{21}$-dicarboxylic acid having the formula

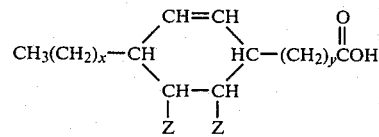

wherein x and y are integers from 3 to 9, x and y together equal 12, Z is a member of the group consisting of hydrogen and COOH, with one Z of each moiety.

9 Claims, No Drawings

$C_{21}$-DICARBOXYLIC ACID ISETHIONATES AS PRIMARY ANIONIC SURFACTANTS

This is a division of application Ser. No. 395,252 filed July 6, 1982, now U.S. Pat. No. 4,476,055.

BACKGROUND OF THE INVENTION (1) Field of the Invention

This invention relates to $C_{21}$-dicarboxylic acid based acyl isethionates and their use as primary anionic surfactants in liquid surfactant systems. The invention also relates to the method of producing the surfactants by the reaction of $C_{21}$-dicarboxylic acid, or a blend of $C_{21}$-dicarboxylic acids and fatty acids, with 2-hydroxyethane sulfonate.

(2) Description of the Prior Art

The fatty acyl isethionates 1 are derived essentially from fatty acid or acid chloride and an alkali metal 2-hydroxyethane sulfonate 2 which in turn is derived from ethylene oxide 3 and an alkali metal bisulfite 4, according to the following reaction sequence.

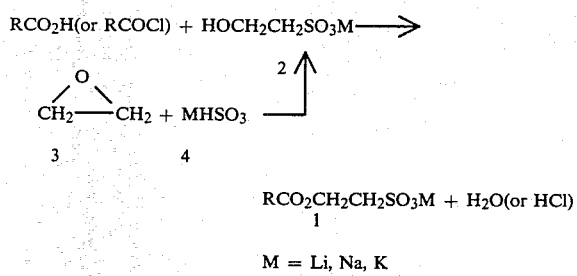

$$M = Li, Na, K$$

Although first prepared and developed in Germany during the 1930's under the general name Igepon A ® (U.S. Pat. No. 1,881,172), the acyl isethionates have never been widely used in heavy duty detergents for several reasons. First, until recently cheaper petroleum-derived anionics were readily available. Second, because of the sulfonate-activated ester linkage, the isethionates are not hydrolytically stable at the high pH's often encountered in heavy-duty laundry products. Third, the isethionates are high melting (above 150° C.), waxy (when made with excess fatty acid) and relatively water insoluble, making it very difficult to prepare and handle them except as more expensive powders. Currently, the Igepon A ® type products are consumed almost exclusively in synthetic toilet soap bars where they provide mildness, hardness and foam (U.S. Pat. No. 4,180,470). For this application the isethionates are made with an excess of fatty acid which drives the reaction to completion. Stearic acid is added and the mixture neutralized with alkali to give the soap, which is formed directly into bars. Handling problems are thus avoided.

In U.S. Pat. No. 3,842,119, 2-hydroxypropane-sulfonate derivatives of $C_{21}$-dicarboxylic acid were prepared as lime soap-dispersing agents. These are different from the isethionates and are prepared with a process requiring epichlorohydrin.

It is the general object of this invention to provide novel $C_{21}$-dicarboxylic acid based acyl isethionates and their salts which are highly water soluble and useful in liquid surfactant systems. Another object of this invention is to provide a process for producing the $C_{21}$-dicarboxylic acid based acyl isethionates.

Other objects, features and advantages of this invention will become apparent from the following description of the preferred embodiments.

SUMMARY OF THE INVENTION

It has been found that novel water-soluble surfactants are prepared by reacting 2-hydroxyethane sulfonate with $C_{21}$-dicarboxylic acid, or a mixture of $C_{21}$-dicarboxylic acid and fatty acids wherein the $C_{21}$-dicarboxylic acid comprises at least 5% by weight of the mixture. The $C_{21}$-dicarboxylic acid has the general formula

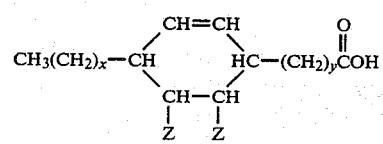

wherein x and y are integers from 3 to 9, x and y together equal 12, Z is a member of the group consisting of hydrogen and COOH, with one Z of each moiety.

DESCRIPTION OF THE PREFERRED EMBODIMENTS

The $C_{21}$-dicarboxylic acids used in this invention are produced from linoleic acid of various animal, vegetable and tall oil sources. The $C_{21}$-dicarboxylic acids may be made by reacting linoleic acid with acrylic acid and catalytic amounts of iodine. One such process for making the $C_{21}$-dicarboxylic acids for use in the esters of this invention is set forth in U.S. Pat. No. 3,753,968 entitled "Selective Reaction of Fatty Acids and Their Separation."

The novel water-soluble surfactants of this invention are prepared by reacting $C_{21}$-dicarboxylic acid, either alone or as comprising at least 5% of a mixture of fatty acids, with an alkali metal, ammonium or substituted ammonium 2-hydroxyethane sulfonate. Since the primary carboxylic acid group is more reactive than the more sterically hindered secondary group, the predominant reaction product is the hemi-isethionate of the formula

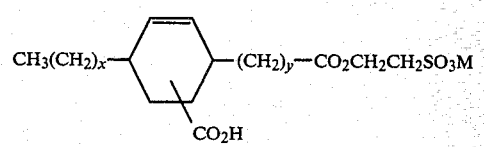

with the primary carboxyl substituted and the secondary carboxyl available for soap formation; although, small amounts of the other hemi-isethionate of the formula

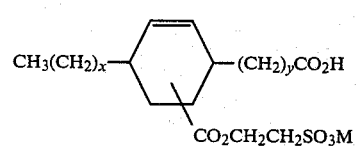

and the bis-isethionate of the formula

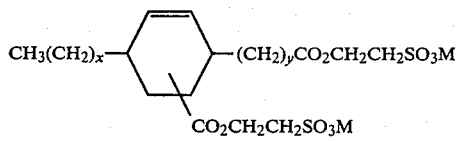

are also produced, wherein, as in all the product formulas, x and y are integers from 3 to 9 and x and y equal 12, and M is an alkali metal cation, such as Li+, Na+ or K+, ammonium or substituted ammonium. Also, M may be an alkaline earth metal cation, such as Ca++ or Mg++, wherein the acyl isethionate has been prepared from the corresponding ammonium isethionate.

Of course, where the $C_{21}$-dicarboxylic acid is present in a mixture of fatty acids, fatty acyl isethionates are also produced by the reaction.

As suggested above, the hemi-isethionates may be subsequently neutralized to soaps the cations of which are selected from the group consisting of Li+, Na+, K+, NH4+, Mg++, Ca++ and substituted amines, such as triethanolamine (HN(CH2CH2OH)3+).

Therefore, the novel hemi-isethionates of this invention are described by the general formula

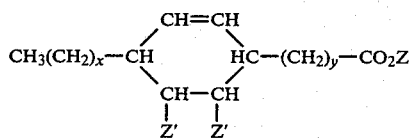

wherein x and y are integers from 3 to 9, x and y together equal 12, Z is selected from the group consisting of hydrogen, CH2CH2SO3M and M', one Z' is hydrogen and the remaining Z' is selected from the group consisting of COOH and COOM' when Z is CH2CH2SO3M, and CO2CH2CH2SO3M when Z is hydrogen or M', where M is an alkali metal cation, alkaline earth metal cation, ammonium or substituted ammonium, and M' is a cation selected from the group consisting of Li+, Na+, K+, NH4+, Mg++, Ca++ and substituted amines. The preferred substituted amine cation is NH(CH2CH2OH)3+.

The novel bis-isethionates of this invention are described by the general formula

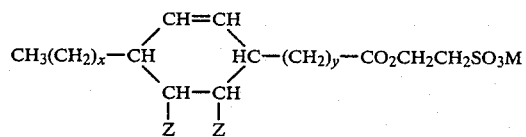

wherein x and y are integers from 3 to 9, x and y together equal 12, one Z is hydrogen and the remaining Z is CO2CH2CH2SO3M, where M is an alkali metal cation, alkaline earth metal cation, ammonium or substituted ammonium.

In the preferred embodiment of the invention $C_{21}$-dicarboxylic acid is reacted with sodium 2-hydroxyethane sulfonate in an equivalent ratio (acid/alcohol) of from about 1.2 to about 2.0, preferably 1.6, using either 0.1% to 3.0%, preferably 1%, p-toluene sulfonic acid, 0.02% to 1.0% phosphoric acid or 0.1% to 1.0% zinc oxide as catalyst. The preferred catalyst is from 0.2% to 0.4% phosphoric acid. A nitrogen sparge is preferably used in place of vacuum, since it gives a product with lower color. The progress of the reaction is monitored by the acid number. The $C_{21}$-dicarboxylic acid isethionate can be spray-dried after diluting with water and neutralizing to pH 7. However, the product is quite soluble in water so it is preferred to merely dilute and neutralize. The $C_{21}$-dicarboxylic acid hemi-isethionate is soluble in water to the extent of 50% solids even at pH 4.2 with only slight haziness. The sodium or potassium soap gives a clear 50–60% aqueous solution at pH 7, and the triethanolamine soap is soluble to the extent of 75%.

Similarly, acyl isethionate anionic surfactants may be prepared by reacting sodium-2 hydroxyethane sulfonate with a mixture of fatty acids comprised of at least 5% $C_{21}$-dicarboxylic acid and at most 95% of a mixture of aliphatic hydrocarbons having from 8 to 20 carbon atoms and including unsubstituted, saturated or unsaturated, straight-chain fatty acids such as lauric acid, myristic acid, palmitic acid, stearic acid, and oleic acid derived from vegetable oils such as palm kernel oil, soybean oil, coconut oil, tallow and/or tall oil.

EXAMPLE 1

A ten-gallon reaction kettle was charged with 20 lb $C_{21}$-dicarboxylic acid (acid number 270, saponification number 304). This was heated with agitation to 60° C.; and a slurry of 8.9 lb 2-hydroxyethane sulfonate in 3 lb water was added. The mixture was heated to 175° C. over one hour while purging with nitrogen during which time the slurry water was driven off. Phosphoric acid catalyst (0.12 lb, 85%) was added and heating continued to a temperature of 240° C. After five hours at this temperature, the acid number had fallen to 87. Heating was stopped and the mixture cooled to 220° C. The nitrogen sparge was discontinued, the gas outlet sealed and 19 lb water pumped into the mixture over 20 minutes. Additional coil cooling brought the temperature to 60° C. at which point the solution was neutralized to pH 7 with a solution of 0.766 lb sodium hydroxide in 8.5 lb water. The resulting solution was agitated a further one-half hour and cooled to room temperature. The solids content was 49%.

The $C_{21}$-dicarboxylic acid based isethionates exhibit very good solubility in water at pH 8 and are easily handled as aqueous concentrates. A 50–60% aqueous solution of the hemi-isethionate soap at pH 7 is clear and stable down to 0° C.

EXAMPLE 2

Sodium 2-hydroxyethane sulfonate was reacted in a similar manner with a mixture of fatty acids containing approximately 30% $C_{21}$-dicarboxylic acid and approximately 70% of a majority of tall oil-derived monounsaturated fatty acids and a minority of tall oil derived palmitic, stearic and linoleic acids. A reaction kettle was charged with a slurry of 26.75 lb of sodium 2-hydroxyethane sulfonate in 11.5 lb water, 61.5 lb of the fatty acid mixture (acid number 228) and 0.1 lb phosphoric acid catalyst. The mixture was agitated and heated to 235° C. over 3 hours with a nitrogen sparge. During this time the slurry water was driven off. The temperature was maintained for 4 hours after which time the acid number had fallen to 85. The mixture was cooled to 205° C., the sparge discontinued, the gas outlet sealed, and 105 lb water pumped in over one-half hour. The mixture was cooled to 60° C. and neutralized to pH 7.5 with a solution of 2.45 lb sodium hydroxide in 4.7 lb water. The resulting solution had a solids content of 44%.

The mixed fatty acid isethionates may exhibit some hazing or titering at 25° C. or below for 45% aqueous solutions at pH 8. The extent of hazing depends upon several factors. Despite possible hazing, isethionate slurries remain fluid and pumpable at room temperature at a solids content of even greater than 50%.

EXAMPLE 3

The anionic surfactant performance of the isethionates prepared according to the procedures of Examples 1 and 2 was evaluated in liquid detergent formulations and found to be superior to that of the anionic surfactant linear alkylbenzene sulfonate in the same systems.

Detergency and redeposition data for clay-soiled fabric were obtained using the following material, equipment and conditions:

Fabric (Scientific Services clay-soiled swatches, Cotton 400 Lot #1579, Cotton/Polyester 7406 WRL Lot #1577, Polyester 767 Lot #1578);

Terg-O-Tometer (United States Testing Company, Hoboken, N.J.);

100° F.; 150 ppm hardness (Ca:Mg 2:1); 1.7 grams liquid detergent (30% active)/bucket; 10 min wash cycle; 5 min rinse cycle; dryer dried; and swatches read 8 ply on Gardner XL 800 Colorimeter with filter on.

Each formulation was tested in five wash cycles. For each cycle two 4×6 inch soiled swatches of each fabric type were washed along with the two unsoiled redeposition swatches of each type. Soiled swatches wee replaced with new ones between cycles and read after the first, third and fifth cycles, while the redeposition swatches from the first cycle were used again in all subsequent cycles and read after the fifth cycle.

The table gives results for detergency and redeposition on clay-soiled cotton, cotton/polyester and polyester fabrics. Detergency relates to the ability of a surfactant system to remove soil from the fabric and redeposition to the ability to suspend that soil and prevent it from redepositing onto clean (especially white) fabric. This is also referred to as whiteness retention. Detergency is evaluated from reflectance measurements on soiled swatches which become whiter during the wash cycle and redeposition from measurements on clean swatches, included in the wash batch, which become soiled during the wash cycle.

| | DETERGENCY AND REDEPOSITION ON CLAY-SOILED FABRIC | | | | | |
|---|---|---|---|---|---|---|
| | Detergency (3 Cycles) | | | Redeposition (After 5 Cycles) | | |
| Detergent | Cotton | Cotton/ Polyester | Polyester | Cotton | Cotton/ Polyester | Polyester |
| Linear alkylbenzene sulfonate | 57.1 | 59.8 | 67.1 | 40.8 | 38.7 | 56.3 |
| $C_{21}$—dicarboxylic acid isethionate | 59.8 | 63.4 | 66.8 | 47.5 | 37.4 | 52.7 |
| Mixed fatty acid isethionate | 58.4 | 63.9 | 66.8 | 47.2 | 39.4 | 57.7 |

The data in the table are in reflectance units, and differences of one or more units can be distinguished by the human eye. The isethionates perform equal or superior to linear alkylbenzene sulfonate as primary anionic surfactants.

While the invention has been described and illustrated herein by references to various specific materials, procedures and examples, it is understood that the invention is not restricted to the particular materials, combinations of materials, and procedures selected for that purpose. Numerous variations of such details can be employed, as will be appreciated by those skilled in the art.

What is claimed is:

1. A process for preparing hemi-isethionates of the formula

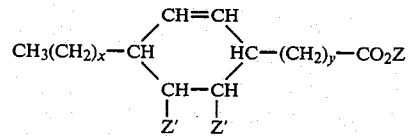

wherein x and y are integers from 3 to 9, x and y together equal 12, Z is selected from the group consisting of hydrogen and $CH_2CH_2SO_3M$, one $Z'$ is hydrogen and the remaining $Z'$ is COOH when Z is $CH_2CH_2SO_3M$, and $CO_2CH_2CH_2SO_3M$ when Z is hydrogen, where M is selected from the group consisting of alkali metal cation, alkaline earth metal cation and ammonium cation, which comprises reacting, in an inert environment, a hydroxyethane sulfonate selected from the group consisting of alkali metal, alkaline earth metal and ammonium 2-hydroxyethane sulfonate with $C_{21}$-dicarboxylic acid of the formula

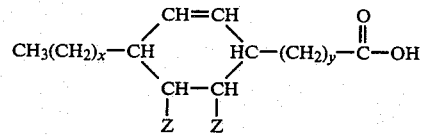

wherein x and y are integers from 3 to 9, x and y together equal 12, one Z is hydrogen and the remaining Z is COOH, at a temperature between 180° C. to 260° C. for from 1 to 10 hours in an acid:alcohol equivalent ratio of from 1.2 to 2.0 in the presence of a catalytic amount of a member of the group consisting of phosphoric acid, p-toluene sulfonic acid and zinc oxide.

2. The process of claim 1 wherein the $C_{21}$-dicarboxylic acid reactant is provided by a mixture of fatty acids comprised of at least 5% as $C_{21}$-dicarboxylic acid and at most 95% as a mixture of aliphatic hydrocarbons having from 8 to 20 carbon atoms and including unsubstituted, saturated and unsaturated, straight-chain fatty acids.

3. The process of claim 3 wherein the aliphatic hydrocarbons are derived from at least one member of the group consisting of soybean oil, palm kernel oil, coconut oil, tallow and tall oil.

4. The process of claim 3 wherein the aliphatic hydrocarbons are derived from tall oil.

5. The process of claim 4 wherein the mixture of fatty acids consists essentially of approximately 30% $C_{21}$-dicarboxylic acid and approximately 70% of a majority of monounsaturated fatty acids and a minority of palmitic acid, stearic acid and linoleic acid.

6. The process of claim 1 or 2 wherein the inert environment is provided by a vacuum or a nitrogen or carbon dioxide sparge.

7. The process of claim 1 or 3 wherein the catalytic amount of p-toluene sulfonic acid is from 0.1% to 3.0%, the catalytic amount of phosphoric acid is from 0.02% to 0.5% and the catalytic amount of zinc oxide is from 0.1 to 1.0.

8. The process of claim 1 or 2 wherein the hemi-isethionates are subsequently neutralized to soaps by the addition of cations selected from the group consisting of $Li^+$, $Na^+$, $K^+$, $NH_4^+$, $Mg^{++}$, $Ca^{++}$, and substituted amines, producing a product of the general formula

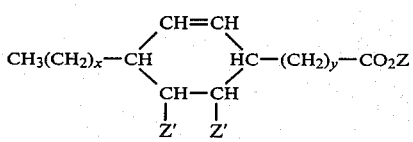

wherein x and y are integers from 3 to 9, x and y together equal 12, Z is selected from the group consisting of $CH_2CH_2SO_3M$ and M', one Z' is hydrogen and the remaining Z' is COOM' when Z is $CH_2CH_2SO_3M$, and $CO_2CH_2CH_2SO_3M$ when Z is M', where M is an alkali metal cation, alkaline earth metal cation or ammonium, and M' is a cation selected from the group consisting of $Li^+$, $Na^+$, $K^+$, $NH_4^+$, $Mg^{++}$, $Ca^{++}$ and substituted amines.

9. The process of claim 8 wherein the substituted amine cation is $HN(CH_2CH_2OH)_3^+$.

* * * * *

UNITED STATES PATENT AND TRADEMARK OFFICE
CERTIFICATE OF CORRECTION

PATENT NO. : 4,514,335
DATED : April 30, 1985
INVENTOR(S) : Richard B. Du Vernet It is certified that error appears in the above-identified patent and that said Letters Patent is hereby corrected as shown below:

In column 5, line 33, "wee" should read --were--.

In column 6, line 57, in claim 3, "claim 3" should read --claim 2--.

In column 7, line 6, in claim 7, "claim 1 or 3" should read --claim 1 or 2--.

Signed and Sealed this

Twentieth Day of August 1985

[SEAL]

Attest:

DONALD J. QUIGG

Attesting Officer     Acting Commissioner of Patents and Trademarks